United States Patent [19]
Javitt et al.

[11] Patent Number: 5,494,901
[45] Date of Patent: Feb. 27, 1996

[54] TOPICAL COMPOSITIONS FOR THE EYE COMPRISING A β-CYCLODEXTRIN DERIVATIVE AND A THERAPEUTIC AGENT

[76] Inventors: Jonathan C. Javitt, 3800 Reservoir Rd., NW., Washington, D.C. 20007; Norman B. Javitt, 501 E. 79th St., New York, N.Y. 10016; Peter McDonnell, 1450 San Pablo St., Los Angeles, Calif. 90033

[21] Appl. No.: 935
[22] Filed: Jan. 5, 1993
[51] Int. Cl.⁶ ............ A61K 31/715; A61K 31/70
[52] U.S. Cl. .......... 514/58; 514/230.5; 514/363; 514/912; 514/913; 514/914; 514/915; 536/103
[58] Field of Search ........... 514/58, 230.5, 514/363, 912, 913, 914, 915; 536/103

[56] References Cited

U.S. PATENT DOCUMENTS

| | | | |
|---|---|---|---|
| 4,371,673 | 2/1983 | Pitha | 536/112 |
| 4,383,992 | 5/1983 | Lipari | 514/58 |
| 4,438,123 | 3/1984 | Smith | 514/58 |
| 4,474,811 | 10/1984 | Masuda et al. | 562/492 |
| 4,596,795 | 6/1986 | Pitha | 514/58 |
| 4,619,939 | 10/1986 | Maren | 514/363 |
| 4,642,305 | 2/1987 | Johansson et al. | 514/178 |
| 4,727,064 | 2/1988 | Pitha | 514/58 |
| 4,764,604 | 8/1988 | Müller | 536/103 |
| 4,822,819 | 4/1989 | DeSantis et al. | 514/530 |
| 4,824,866 | 4/1989 | Kuam | 514/601 |
| 4,888,168 | 12/1989 | Potts et al. | 514/912 |
| 4,975,428 | 12/1990 | Shell | 514/230.5 |
| 4,983,586 | 1/1991 | Bodor | 514/58 |
| 5,002,935 | 3/1991 | Bodor | 514/58 |
| 5,011,843 | 4/1991 | Shell | 514/259 |
| 5,024,998 | 6/1991 | Bodor | 514/58 |
| 5,049,587 | 9/1991 | Okamoto et al. | 514/913 |
| 5,212,162 | 5/1993 | Missel et al. | 514/58 |
| 5,324,718 | 6/1994 | Loftsson | 514/58 |

FOREIGN PATENT DOCUMENTS

| | | |
|---|---|---|
| 1222697 | 6/1987 | Canada . |
| 0082921 | 7/1983 | European Pat. Off. . |
| 213514 | 3/1987 | European Pat. Off. . |
| 0286791 | 10/1988 | European Pat. Off. . |
| 294239 | 12/1988 | European Pat. Off. . |
| 326196 | 8/1989 | European Pat. Off. . |
| 0335545 | 10/1989 | European Pat. Off. . |
| 338507 | 10/1989 | European Pat. Off. . |
| 400637 | 12/1990 | European Pat. Off. . |
| 435682 | 7/1991 | European Pat. Off. . |
| 472327 | 8/1991 | European Pat. Off. . |
| WO82/00096 | 1/1982 | WIPO . |
| WO85/01875 | 5/1985 | WIPO . |
| WO85/02767 | 7/1985 | WIPO . |
| WO91/11200 | 8/1991 | WIPO . |

OTHER PUBLICATIONS

Strattan, C. E., Pharmaceutical Technology, Jan. 1992, pp. 69–74.
Grove et al., Chemical Abstracts, CA116: 27958u. (1990).
Jansen et al., Chemical Abstracts, CA115: 15428n. (1990).

*Primary Examiner*—Ronald W. Griffin

[57] ABSTRACT

A topical composition comprising an amount of a carbonic anhydrase inhibitor and an amount of β-cyclodextrin derivative effective in increasing the bioavailability of the carbonic anhydrase inhibitor when coadministered topically to the eye.

29 Claims, 2 Drawing Sheets

TOPICAL COMPOSITIONS FOR THE EYE COMPRISING A β-CYCLODEXTRIN DERIVATIVE AND A THERAPEUTIC AGENT

BACKGROUND OF THE INVENTION

This invention relates to compositions of an active agent and a β-cyclodextrin derivative which are topically effective in treating eye conditions.

Glaucoma is a degenerative disease of the eye characterized by optic nerve loss, often in a characteristic nerve fiber bundle configuration. If untreated, glaucoma will eventually lead to blindness. More than 1% of Americans over the age of 40 suffer from this potentially blinding condition. Black Americans are 4 times more likely to suffer from glaucoma and 6–8 times more likely to be blind from glaucoma than are white Americans. The most important risk factor for glaucomatous optic nerve damage is elevated intraocular pressure (IOP). Although there is a real, albeit low, risk of glaucoma in persons with normal IOP (i.e., 16 mm Hg), the glaucoma risk in persons with even mild elevation of IOP (i.e., >22 mm Hg) is elevated 10-fold. When IOP is over 28 mm Hg, the glaucoma risk is approximately 40-fold higher than when IOP is normal.

Four major classes of pharmacologic agents are currently employed to lower IOP on a chronic basis: β-adrenergic blockers, miotics, α-adrenergic agonists, and carbonic anhydrase inhibitors. However, none of the currently available pharmacologic agents is entirely satisfactory. At least 10% of glaucoma sufferers require laser and/or incisional surgery, in addition to medical therapy, to achieve adequate control of IOP. Even when pharmacologic control is possible, the side effects of current agents, combined with poor patient compliance, limit their effectiveness.

Miotic agents, of which pilocarpine is the most frequently used, lower IOP by increasing aqueous outflow through the trabecular meshwork of the eye. Although their topical use is associated with minimal systemic side effects, they frequently cause objectionable ocular and periocular effects. Miotic agents generally cause pupillary constriction, which severely diminishes night vision, and also induce myopia (near-sightedness). Often patients will complain of an objectionable headache or browache associated with topical administration of these compounds.

β-adrenergic blocking agents, of which timolol is the most frequently used, lower IOP by decreasing aqueous secretion. At least five different β-adrenergic blockers are in topical use in the United States with comparable effectiveness. A reduction of up to 25% in IOP can generally be expected when starting a patient on therapy with these agents. Although the β-adrenergic blockers have few ophthalmologic side effects, their systemic side effects can be severe, and occasionally fatal. Topically administered ophthalmologic β-adrenergic blockers can have the same spectrum of systemic side effects as those administered orally or parenterally. Presumably this is a function of drainage through the nasolacrimal duct with absorption across the nasal mucosa. Side effects include heart failure, bradycardia, bronchospasm, dizziness, syncope, depression, dementia, and impotence. At least 10% of patients begun on topical β-adrenergic blockers experience one or more of these symptoms, and there is a widely held belief that greater prevalence of these side effects goes unrecognized.

The α-adrenergic agonist class of compounds is best exemplified by epinephrine and related compounds. While they are used topically in the form of eye drops, in general, they exert less of a pressure-lowering effect than other classes of agents. Patients frequently develop sensitivity to epinephrine and dipiviphrine when used for a year or longer.

Although considerable effort has been directed towards developing topically active carbonic anhydrase inhibitors, they are currently available only for systemic use. While extremely effective at lowering pressure, they often cause numbness and tingling, gastrointestinal upset, depression, lethargy, loss of appetite, and general malaise. These, in addition to the occasional severe systemic reaction, such as aplastic anemia, are so common that many physicians are reluctant to routinely prescribe carbonic anhydrase inhibitors for long-term use.

While investigators have long realized the benefits that would accompany topical administration of carbonic anhydrase inhibitors, the selection of the proper coformulation entity has long eluded them. Most reports in the literature indicate that carbonic anhydrase inhibitors are inactive topically because they cannot cross the cornea. See, for example, U.S. Pat. Nos. 4,888,168 (e.g., column 1, lines 30–36), and 4,619,939 (e.g., column 3, lines 50–53). In some cases, even direct injection of carbonic anhydrase inhibitors into the anterior chamber has been shown to have no pressure lowering effect.

Because carbonic anhydrase inhibitors have a profound effect in altering basic metabolism, the avoidance of a systemic route serves to diminish, if not entirely eliminate, those side effects caused by metabolic acidosis such as hypokalemia, numbness, tingling, general malaise, etc.

Silvistrini, "Effects of Topically Instilled Drugs on Intraocular Pressure in Rabbits", *Arzeim.-Forsch. (Drug Res.)* 25, Nr. 5 (1975), teaches that the disodium salts of acetazolamide can be used to lower the intraocular pressure of the normal rabbit eye. Silvestrini and subsequent investigators fail to confront the problem associated with the high pH of disodium salt solutions and the significant probability of severe irritation. Attempts to buffer the solutions to a near-physiologic pH generally lead to precipitation of the metal salt.

On the other hand, there is a large body of disclosure supporting the use of cyclodextrin compounds, especially hydroxypropyl-β-cyclodextrin, as excipients for solubilizing non-polar molecules, including a variety of pharmaceutical agents. Hydroxypropyl-β-cyclodextrin (HPBCD) and its preparation by propylene oxide addition to β-cyclodextrin was described in Gramera et al., U.S. Pat. No. 3,459,791. Gramera et al. specifically teach the use of HPBCD to alter the solubility of desirable guest molecules, such as flavoring agents or pharmaceutical agents (column 6, lines 34–37).

Much more recently, Pitha, U.S. Pat. No. 4,596,795, disclosed that the amorphous nature of particular β-cyclodextrin derivatives contributed to the solubilizing effect. Likewise, Muller et al., WO85/02767, disclosed that hydroxyalkyl ethers of β-cyclodextrin are useful for dissolving sparingly water-soluble drugs and for increasing their bioavailability. All examples of the β-cyclodextrin composition in Muller et al. were low viscosity aqueous solutions of between 5% and 7.5% of the β-cyclodextrin derivative combined with 1% or less of the active agent. Muller et al. specifically teaches (Example 7) that when a 0.75% solution of lidocaine, a highly water-soluble compound is constituted in a 5% or 7.5% solution of hydroxypropyl-β-cyclodextrin, there is an increase in bioavailability, as measured by duration of anesthetic effect.

Jansen et al., *Chemical Abstracts*, CA115(2):15428n, disclose the potential use of β-cyclodextrin derivatives in ophthalmic preparations. Although they found that dimethyl-β-cyclodextrin is toxic to the rabbit corneal epithelium, 12.5% HPBCD was tolerated by the cornea when applied topically. However, when the effect of β-cyclodextrin on the bioavailability of topically administered carbonic anhydrase inhibitor, L-671152, was studied, Grove et al., *Chemical Abstracts*, CA116:27958u, showed that β-cyclodextrin at either 3% or 1.5% reduced ocular bioavailability to about 50% as compared to when the inhibitor was administered alone.

SUMMARY OF THE INVENTION

The present invention provides a method of solubilizing active agents to make them more bioavailable, especially those which are sparingly water-soluble, by combining these agents with β-cyclodextrin derivatives. The combination of active agent and β-cyclodextrin derivative is especially advantageous for topical use in the eye. A carbonic anhydrase inhibitor is a preferred example of an active agent.

The present invention provides an ophthalmic eye drop dispenser comprising a topical, ophthalmic composition comprising an effective amount of a carbonic anhydrase inhibitor and an amount of an amorphous β-cyclodextrin effective in increasing the bioavailability of the carbonic anhydrase inhibitor when coadministered topically to the eye. The present invention also provides an ophthalmic eye drop dispenser comprising a topical, ophthalmic composition comprising an effective amount of a carbonic anhydrase inhibitor and an amount of an amorphous β-cyclodextrin effective in increasing the solubility of the carbonic anhydrase inhibitor in the composition, in comparison to its solubility in the absence of the amorphous β-cyclodextrin.

The present invention also relates to a topical, ophthalmic composition comprising an effective amount of a carbonic anhydrase inhibitor and 40–60 w/v % of an amorphous β-cyclodextrin, said amount of β-cyclodextrin being effective to increase the bioavailability of the carbonic anhydrase inhibitor upon topical administration.

The compositions of this invention are also effective in prolonging the therapeutic effect of the agent when administered to the eye.

The present invention further relates to a method of treating an eye disorder by administering a carbonic anhydrase inhibitor, comprising topically administering to the eye a topical, ophthalmic composition comprising an effective amount of a carbonic anhydrase inhibitor and an amount of β-cyclodextrin derivative, especially hydroxy-propyl-β-cyclodextrin (HPBCD), effective in increasing the bioavailability of the carbonic anhydrase inhibitor when topically administered to the eye. The method can be used to treat intraocular pressure disorders, glaucoma, hypersecretion of fluid by the ciliary body, and other disorders which affect the eye.

The invention especially relates to carbonic anhydrase inhibitors that are hereby for the first time rendered topically effective in the treatment of elevated intraocular pressure. Particularly, it relates to compositions comprising acetazolamide, methazolamide, and related compounds dissolved in a high efficiency preparation of HPBCD. When these preparations are applied topically to the eye, the active agent enters the aqueous humor via the cornea and inhibits the action of carbonic anhydrase in the ciliary body epithelium. The effect of this inhibition is to decrease the carbonic anhydrase-dependent secretion of aqueous humor. Inhibition of aqueous humor production is known to decrease intraocular pressure in many forms of glaucoma and ocular hypertension.

Various other objects, features, and attendant advantages of the present invention will be more fully appreciated as the same becomes better understood when considered in conjunction with the accompanying drawings, in which like reference characters designate the same or similar parts throughout the several views and wherein.

Figure 1:
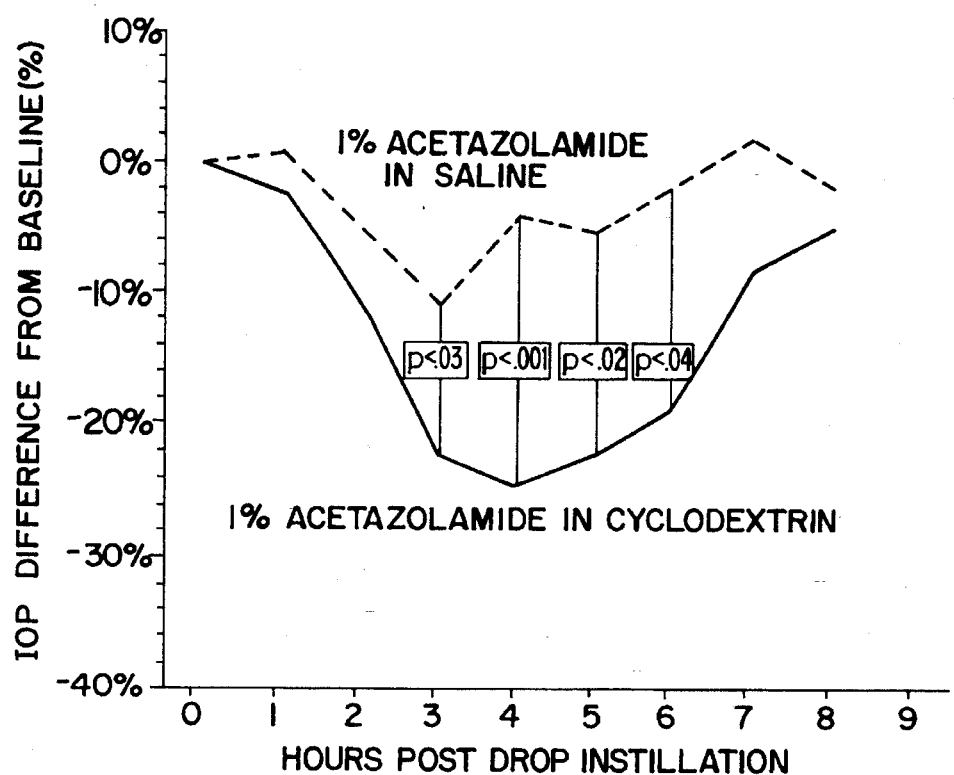
FIG. 1 shows the effect of a 1% acetazolamide solution, alone and in combination with 45% HPBCD, on intraocular pressure (IOP) when administered topically to the eye.

In investigating the ability of various therapeutic agents to reduce intraocular pressure, it has been determined that surprisingly high reductions in intraocular pressure can be achieved when the therapeutic agent is coadministered with certain β-cyclodextrin derivatives. The reduction in intraocular pressure is much greater than expected when the agent is administered topically to the eye alone. These novel and surprising results contradict the current teachings and enable the formulation of novel therapeutic compositions comprising β-cyclodextrin derivatives for topical use in the eye. In particular, a composition comprising a carbonic anhydrase inhibitor and hydroxypropyl-β-cyclodextrin (HPBCD) is unexpectedly efficacious in reducing intraocular pressure when administered to the eye, despite the inability of the prior art to successfully formulate these active ingredients for topical administration.

The compositions of the present invention comprise a β-cyclodextrin derivative and an active agent, formulated together for topical administration to the eye. The invention provides a useful and efficient way of administering agents to the eye for diagnostic, prophylactic, and therapeutic uses. Sparingly water-soluble therapeutic agents are especially benefitted, including those which heretofore were not administrable to the eye. The compositions can be used in the treatment of any animal, e.g., horses, cows, rabbits, dogs, cats, birds, etc., especially mammals, including humans. Typically, they are provided in an ophthalmic eye-drop dispenser for topical delivery to the eye, e.g., a squeeze bottle, a bottle/dropper combination, an eye dropper, etc. However, any topical ophthalmic applicator may comprise the composition of this invention, including conventional ophthalmic inserts, implants, ointments, salves, polymers, gels, and the like. See, e.g., *Physicians' Desk Reference for Ophthalmology* (1982 Edition), published by Medical Economics Company, Inc., Oridell, N.J.; see, e.g., pages 112–114.

A composition comprising a carbonic anhydrase inhibitor and a β-cyclodextrin derivative is a preferred embodiment of the present invention. In particular, the carbonic anhydrase inhibitor is a sulfamide, including, e.g., a heterocyclic sulfamide or alkali metal salts thereof, as disclosed in U.S. Pat. No. 4,438,123; compounds of U.S. Pat. No. 4,619,939, such as 2-orthochlorophenylthiadiazole-5-sulfonamide or 2-trifluoroacetylimino-3-methyl-$\Delta^2$- 1,3,4-thiadiazoline-5-sulfonamide; methazolamide analogs of U.S. Pat. Nos. 4,636, 515 and 5,104,887; compounds of U.S. Pat. No. 4,975,446; compounds of U.S. Pat. No. 5,055,480; prodrugs of U.S. Pat. No. 5,095,026, such as 2-benzothiazolesulfonamide; and the carbonic anhydrase inhibitor L-671152 of Grove et al., *Chemical Abstracts*, CA116:27958u. Especially preferred are acetazolamide and methazolamide.

The carbonic anhydrase inhibitor is present in the composition at a dosage which is able to achieve the desired therapeutic effect, e.g., lowering intraocular pressure. Typically, this is about 0.1 to about 3.5 w/v %, the precise amount not being critical and lower and higher amounts being possible. For acetazolamide and methazolamide, the preferred range is about 1 to about 2 w/v %.

Whereas this disclosure is written primarily in terms of carbonic anhydrase inhibitors, the invention (especially the "high efficiency" aspects discussed below) is applicable to any agent whose bioavailability (in level of effect, duration of effect, etc.), or solubility, is desirably increased, including especially agents for topical administration, most especially active agents desirably administered to the eye. Such active agents include any agent, such as those described, e.g., in U.S. Pat. No. 4,983,586, e.g., especially those at columns 14 and 15. Particularly useful with respect to the eye are steroids, β-adrenergic blockers, α-adrenergics, prostaglandins, and others discussed, e.g., in texts such as *Physicians' Desk Reference for Ophthalmology, supra*. These are all employable in conventional amounts or, in many cases, lower amounts in view of the enhanced effects achieved by this invention, said amounts being determined routinely. Another advantage of the unique combination of carbonic anhydrase inhibitor, such as acetazolamide, and β-cyclodextrin derivative is that it may be administered in combination with oral and/or parenteral therapy, permitting lower oral/parenteral doses of acetazolamide or other carbonic anhydrase inhibitor to be used, thereby ameliorating adverse side effects of the active agents.

β-cyclodextrin derivatives useful for the present invention are those which are intrinsically amorphous, soluble in hydrophilic solvents, e.g., water soluble, and capable of forming inclusion compounds (guest-host compounds) with active agents which typically are hydrophobic organic molecules, including diagnostic, therapeutic, prophylactic, etc. agents. "Amorphous" has the meaning given in U.S. Pat. Nos. 4,596,795; 4,727,064; and WO 85/02767. The amorphous β-cyclodextrins typically are substituted, e.g., by alkyl, hydroxyalkyl, etc. groups, as described in U.S. Pat. Nos. 3,459,795; 4,727,064; and 4,983,536 and WO 85/02767, by sulfoalkyl groups, as described in U.S. Pat. No. 5,134,127, etc. Any other substituted β-cyclodextrin can also be used in this invention. Typically, amorphous β-cyclodextrin samples will comprise at least two, and usually three or more, different molecules which differ in degree and/or nature of substitution. The derivatives can be prepared by any of the conventional methods disclosed in the aforementioned patents. The hydroxypropyl-β-cyclodextrins (HPBCD) are especially preferred in the topical compositions of the present invention. However, HPBCD includes all analogous β-cyclodextrins containing at least one hydroxypropyl substituent and optionally other moieties.

The β-cyclodextrin derivative, especially HPBCD, increases the bioavailability of the agent when applied topically to the eye. It is especially useful for increasing the bioavailability of agents which are sparingly soluble in water. By "bioavailability," it is meant the degree to which a drug or agent becomes available to the target tissue after its administration to an animal. Thus, an amount of an agent is more available to the eye when it is administered in combination with the amorphous β-cyclodextrin than when that same amount of agent is administered alone or with a different, e.g., lower, concentration of β-cyclodextrin. As a consequence of the increase in bioavailability, e.g., therapeutically effective concentrations of a desired drug are attained in the eye tissue which otherwise could not be achieved, e.g., because of low drug solubility or other reasons. Alternatively, the increased bioavailability permits administration of a lower dosage of the agent than otherwise required in its absence and may be used in conjunction with oral and/or parenteral therapy.

The amount of β-cyclodextrin derivative used in the present invention is effective in increasing the bioavailability of a desired agent when coadministered to the eye. Generally, the solubility of the agent in a solvent, including an aqueous or hydrophilic solvent or a hydrophobic gel, e.g., as used on skin, is also increased. Usually aqueous or alcoholic, e.g., ethanolic, systems are employed, optionally including other water-soluble components, as disclosed herein. The amount of β-cyclodextrin derivative is generally in the range of about 35 to about 95 w/v %, preferably 40–60 w/v %, especially for carbonic anhydrase inhibitors, lower and even higher amounts being possible, e.g., 20, 25, 30, 96, etc. w/v % (95 w/v %=95 g diluted to 100 ml). The relatively high content of the β-cyclodextrin derivative is a surprising aspect of this invention in that the prior art noted decreased bioavailability of active agents upon coformulation with lesser amounts of β-cyclodextrins.

In terms of viscosity of aqueous formulation, the amount of β-cyclodextrin can be that sufficient to achieve a viscosity of about four to ten times more than that of water. Generally, the amount of β-cyclodextrin derivative will be that achieving an increase in bioavailability of active agent (compared to a simple aqueous solution of the active agent) of at least about 10%, preferably higher, e.g., 20%, 25%, 50%, or 100%, and most preferably, e.g., two- to ten-fold or higher or increasing the maximum solubility of the agent (same basis) by similar amounts.

By "coadministered," it is meant that the β-cyclodextrin derivative and agent are provided to the target tissue (e.g., the eye) together via administration as a single composition. However, it is within the scope of this invention to administer the agent and β-cyclodextrin derivative individually and essentially concurrently. The precise amount of a β-cyclodextrin derivative effective in increasing bioavailability for a particular application and agent can be routinely determined conventionally, e.g., by performing a simple series of parametically varied experiments comparing ability of an amount of agent to enter the eye tissue. Example 1 provides one possible visual method of determining bioavailability, and Example 2 provides a possible physiological method of determining bioavailability. More precise methods are routine, e.g., involving measurements of parameters with the most sensitive methods and equipment available.

The solubility of the active agent can be determined by any of the conventional methods available. For example, solutions of the agent, prepared with and without a β-cyclodextrin derivative, can be filtered (e.g., using a 0.22 or 0.45 μm membrane filter) to eliminate undissolved agent, and subjected to chromatography (e.g., reverse-phase HPLC) to determine the concentration of agent present in the solution.

When the β-cyclodextrin derivative is coadministered to the eye with an active agent in amounts which are effective to increase the agent's bioavailability, the amount of β-cyclodextrin is also effective in prolonging the active effect (therapeutic, prophylactic, etc.) of the agent. The ability to prolong an agent's bioactivity is especially advantageous because, e.g., it permits such agents to be administered less frequently than otherwise required. By prolongation of the effect, it is meant that the duration of time during which an agent is active (i.e., biologically, therapeutically, etc.) is increased when it is coadministered with a β-cyclodextrin derivative. The quantity of time by which the β-cyclodextrin derivative "prolongs" the effect of the agent, e.g., the carbonic anhydrase inhibitor, is not critical because any improvement in the time period during which an agent is therapeutically effective in the eye is beneficial. For example, the composition of a carbonic anhydrase inhibitor, e.g., acetazolamide or methazolamide, and a β-cyclodextrin derivative, e.g., HPBCD, reduces intraocular eye pressure topically for a longer period of time as compared to the carbonic anhydrase inhibitor topically administered by itself. By way of illustration, Example 2 (see FIG. 1, especially) shows that hours after the reduction in intraocular pressure caused by acetazolamide, alone, has returned to normal, the intraocular pressure of eyes treated with acetazolamide and HPBCD is still reduced.

The combination of an agent, e.g., a carbonic anhydrase inhibitor such as acetazolamide or methazolamide, and a β-cyclodextrin derivative can be prepared routinely conventionally, e.g., by mixing the two ingredients together by, e.g., stirring, sonicating, vortexing, shaking, or heating.

The agents of this invention are administered conventionally as the same, or analogous active agents otherwise formulated are administered, e.g., topically to achieve a desired effect, except conventionally taking advantage of the benefits of this invention, e.g., employing lower dosages, less frequent administration, etc. The pharmaceutical composition of the present invention can thus be administered as a fluid by any conventional method of delivering drop formulation to an eye such as by means of an ophthalmic eye-drop dispenser capable of delivering a unit dosage. A typical volume of a therapeutic drop is about 1/20 ml. Each administration typically involves 1–2 drops but can be more or less, depending on the concentration of the agent in the composition; and, typically, there are 1–4, usually 3 or 4, administrations per day, all routinely determinable. The drops are typically instilled in the inferior cul-de-sac of the eye. A typical dose of carbonic anhydrase inhibitor according to the present invention will be about 3–4 mg/day topically (e.g., for acetazolamide or methazolamide), which, compared to the oral doses for these two agents (1000 mg and 150 mg per day, respectively), dramatically illustrates an advantage of this invention.

A preferred example of the present invention is a preparation of acetazolamide, methazolamide, or a related carbonic anhydrase inhibitor and HPBCD. When high viscosity solutions of HPBCD (i.e., 35 w/v % or higher) are prepared, topically active compositions are formulated that provide significant, sustained, reductions in intraocular pressure with a single administration. These preparations are also stable, non-irritating, and non-toxic.

The topical composition of the present invention can further comprise conventional additives, including, e.g., preservatives, solvents, viscosity formers, anti-microbial agents, tissue compatibility enhancers (e.g., cholesterol), salts, buffers, surfactants, and other conventional compounds typically employed in formulations for the given topical use, e.g., in the eye. The solutions of the invention are also sterile or non-sterile as desired. These commonly employed additives are fully conventional and are described, e.g., in the *Physician's Desk Reference for Ophthalmology, supra*.

The β-cyclodextrin derivatives of the present invention are preferably those forming a high efficiency composition. The "efficiency" of a composition comprising "guest" (i.e., the active agent) and "host" (i.e., the β-cyclodextrin derivative) molecules is defined herein as the molar ratio between the two, guest/host. Thus, a "high efficiency" β-cyclodextrin derivative will contain (or be capable of containing) more molecules of an active agent than a "low efficiency" β-cyclodextrin derivative. Although both low and high efficiency β-cyclodextrin derivatives are encompassed herein by the term "β-cyclodextrin derivative," and therefore are in the scope of the present invention, the high efficiency derivatives are preferred since they permit solutions having a higher w/v percentage of active agent to be prepared and thus enhance the invention. A particularly preferred high efficiency β-cyclodextrin derivative is HPBCD capable of containing 1.8 w/v % or more of acetazolamide.

High efficiency β-cyclodextrins can be defined herein to be those having a guest/host molar ratio of at least 0.6, preferably at least 0.85, and most preferably at least 1 for compounds such as azetazolamide with relatively high molecular weights, e.g., about 220 or greater. For smaller molecules, e.g., molecular weights less than about 220, more entities can fit in a single cavity, whereby preferred ratios are up to 3:1, for example. It is possible that commercially available samples of β-cyclodextrins will be high efficiency; however, as shown below in Example 3, efficiency can vary. Fortunately, it has now been discovered that efficiency can be increased for a given sample of an amorphous β-cyclodextrin by a routine separation/concentration procedure as discussed below.

Since efficiency is defined as the ratio of guest to host molecules, the more guest molecules contained within the host cavity, the higher the efficiency for the amorphous mixture. For water and other small molecules, more than one guest molecule may fit in the host cavity, and a ratio greater than 1 can be achieved. However, for larger guest molecules, where only one molecule fits inside the host cavity, ratios of less than 1 have been found to occur. This implies that not all the β-cyclodextrin molecules within a given amorphous mixture function as hosts.

For example, for larger molecules such as phenolphthalein (mol. wt.=550) only one molecule is conventionally expected to "fit" in the "cavity" of the cyclodextrin; therefore, the theoretical ratio is 1/1, or equivalent to an efficiency of 1. Since a major use of cyclodextrins per this invention is to solubilize higher molecular weight compounds that have very limited solubility in water, the use of the higher molecular weight phenolphthalein, because of its ease of detection, is suitable as an index of the guest/host ratio for analogous molecules. Other readily detectable compounds can similarly be employed. According to the thrust of the literature, ratios are implied to be 1/1. It is further implied that this ratio remains approximately the same for the 2-hydroxypropyl-β-cyclodextrins, the major type of cyclodextrins proposed for pharmaceutical use because of their much higher water solubility as compared with unmodified β-cyclodextrins and other modified variants.

These principles have been applied to three commercially available samples of 2-hydroxypropyl-β-cyclodextrin prepared by the three different manufacturers. It has been discovered that the manufacturing processes greatly lower efficiencies and that efficiency is guest dependent. The low efficiencies of many currently available 2-hydroxypropyl-β-cyclodextrins are a deterrent to their use in the pharmaceutical industry at least because of the large amount of vehicle that must be administered to deliver a therapeutic concentration of drug, when a therapeutic effect can be attained at all.

Thus, methods have been developed for improvement in efficiency to enhance the use of these compounds for beneficial drug delivery in the treatment of disease.

Examples 3, 6, and 7 illustrate the advantageous nature of utilizing high efficiency β-cyclodextrins in conjunction with this invention.

As can be seen from Example 6, at maximum saturation of phenoltetrabromphthalein, the molar guest/host ratio is much less than theoretical indicating that many of the host molecules have cavities that are not available to guest molecules. Moreover, availability of a cavity to one species of guest molecule such as phenoltetrabromphthalein is not an indication of availability to other molecules such as cholesterol. Thus, the ratio can vary from source to source of β-cyclodextrin and from guest to guest for a given β-cyclodextrin. These findings confirm those of Example 3, wherein the guest/host ratios for each of sources A, B, and C, respectively, are 0.007, 0.008 and 0.011.

Fortunately, it has been discovered that efficiency of a β-cyclodextrin can be enhanced. Such enhanced (high efficiency) β-cyclodextrins are preferred for use in this invention.

Referring to Example 7, palmitic acid is one of many hydrophobic compounds with a density less than that of water which can function as a guest molecule. Displacing water from the cavity of host molecules dissolved in water with palmitic acid will result in the formation of a host-guest complex with a density less than that of the water-filled host molecule. These species complexes of differential densities can then be separated, e.g., by centrifugation as shown in Example 7. The greater amount of palmitic acid in the upper fraction of Example 7 establishes that displacing the heavy water with a compound that has a lower density makes possible the physical separation of those cyclodextrin molecules that can accommodate guest molecules from those that cannot. Harvesting the upper layer therefore provides a fraction of the original β-cyclodextrin sample that has a higher efficiency, i.e., higher ratio of guest to host molecules. Separation of the harvested β-cyclodextrin from the molecule in its cavity can be routinely performed using any applicable conventional technique such as extraction, solubilization/precipitation, volatilization, chromatography, dialysis, and the like. For example, palmitic acid can be extracted by partitioning between ethyl acetate and water, and the more efficient cyclodextrin can be recovered by lyophilization of the aqueous phase.

Thus, in a preferred aspect, this invention employs a β-cyclodextrin which has been pretreated to enhance the guest/host ratio for a given active agent when a given sample of β-cyclodextrin (e.g., 2-hydroxypropyl β-cyclodextrin) has a guest/host ratio which is desirably increased. For example, were the active agent to be palmitic acid, the process of Example 7 could analogously be employed to provide a high efficiency β-cyclodextrin with respect to such active agent. For other active agents having a density different from that of water, analogous centrifugation processes can be used. Of course, where desired, the process can be sequentially applied to the separated high efficiency fraction of a prior iteration until further increases are negligible or a desired efficiency ratio is achieved. Where a density differential does not exist with respect to water for a given active agent, density-based procedures can still be employed using, e.g., solvents other than water, e.g., solutions of water and alcohol, other pure polar solvents, and the like. Alternatively, a given β-cyclodextrin can be rendered more efficient by separation procedures based on a different agent but one which behaves similarly with respect to solubilization by β-cyclodextrin's, e.g., based on results of a few preliminary orientation experiments involving solubility as a function of β-cyclodextrin amount, temperature, etc. Typically, such an analogous agent will have size, shape, polarity, etc. properties similar to that of the agent whose density is the same as or similar to that of water. Such use of an analogous agent of course can always be used even where separation procedures are available for a given agent.

It is also possible that any other physical or chemical property differential between the solvent guest molecule (typically water) and the desired "active" agent guest molecule can be used as the basis for a separation technique to concentrate high efficiency β-cyclodextrin from a mixture of β-cyclodextrin overall having a lower efficiency. Such properties include: electrical (e.g., charge), magnetic (e.g., presence of metal ions), chromatographic, chemical, optical, etc., e.g., even if only with respect to guest molecule portions protruding from the host cavities. Thus, corresponding modalities can be used to effect the separation, e.g, electrophoresis, magnetic fields, chromatography, chemical treatments followed by conventional separation or extraction, extraction per se, optical resolution, etc.

Another strategy for the preparation of high efficiency cyclodextrins is to employ the general principle of affinity chromatography. Thus, a column can be prepared having attached a support or molecule which is to be the guest or an analogous "agent", as described above. Attachment can be through any of the conventional methods, e.g., esterification, amidation, etc. Passage of a sample of β-cyclodextrin through the column will cause the subportion of the latter having the best host characteristics for the bound molecule to be retarded more greatly, thus concentrating the subportion on the column. Routine techniques can be employed to separate the β-cyclodextrin from the column. In one example, a column can employ a 3-β-hemisuccinoyloxycholest-5-ene-N-succimidyl ester to a support. As an aqueous solution of hydroxypropyl-β-cyclodextrin passes through the column, those molecules that can accept cholesterol in their hydrophobic cavity will be retarded and can be harvested separately, either by elution with ethanol or collection as a late fraction from the aqueous wash.

All such β-cyclodextrins produced by such methods are usable in this invention. All will normally be amorphous since it is unlikely that a given resultant high efficiency β-cyclodextrin will comprise only β-cyclodextrins all having the same chemical structure. However, where such a homogeneous β-cyclodextrin is prepared which retains the desired high efficiency properties it is included within the scope of the invention as an "amorphous" β-cyclodextrin, especially where any resultant properties, e.g., crystallinity-based, are not disadvantageous.

As can also be seen above, the term "high efficiency" β-cyclodextrin will include any β-cyclodextrin as long as it has a high guest/host ratio associated therewith for a given guest, irrespective of whether the ratio exists for a β-cyclodextrin mixture prepared conventionally, e.g., commercially available, one of which is prepared by the new efficiency enhancement methods described herein.

While the foregoing has been directed primarily to β-cyclodextrins, the principles of preparation high efficiency versions thereof can be directly applied to other cyclodextrins such as α- or β-cyclodextrins using, e.g., guest molecules appropriate for such hosts.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited herein, are hereby incorporated by reference.

EXAMPLES

Example 1

Solutions of 2% Na-Fluorescein were prepared in 0.9% Saline, 4.5% HPBCD, and 45% HPBCD (the HPBCD is Type B of Example 3). Each solution was applied to the eye of a New Zealand white rabbit and observed for a period of one hour. The anterior chamber of the eye was examined with a standard blue light source on a slit lamp biomicroscope. As expected, considerable fluorescence was seen in the eye receiving 0.9% saline (control eye) at one hour. In contrast, only minimal fluorescence was observed in the eye receiving the 4.5% cyclodextrin preparation. The eye receiving the 45% cyclodextrin preparation had fluorescence equal to or greater than that observed in the control eye and the fluorescence persisted longer than in the control eye. This example indicates that, while a low viscosity solution of HPBCD may decrease bioavailability of a pharmaceutical agent, a high viscosity solution of HPBCD increases bioavailability.

Example 2

Figure 2:
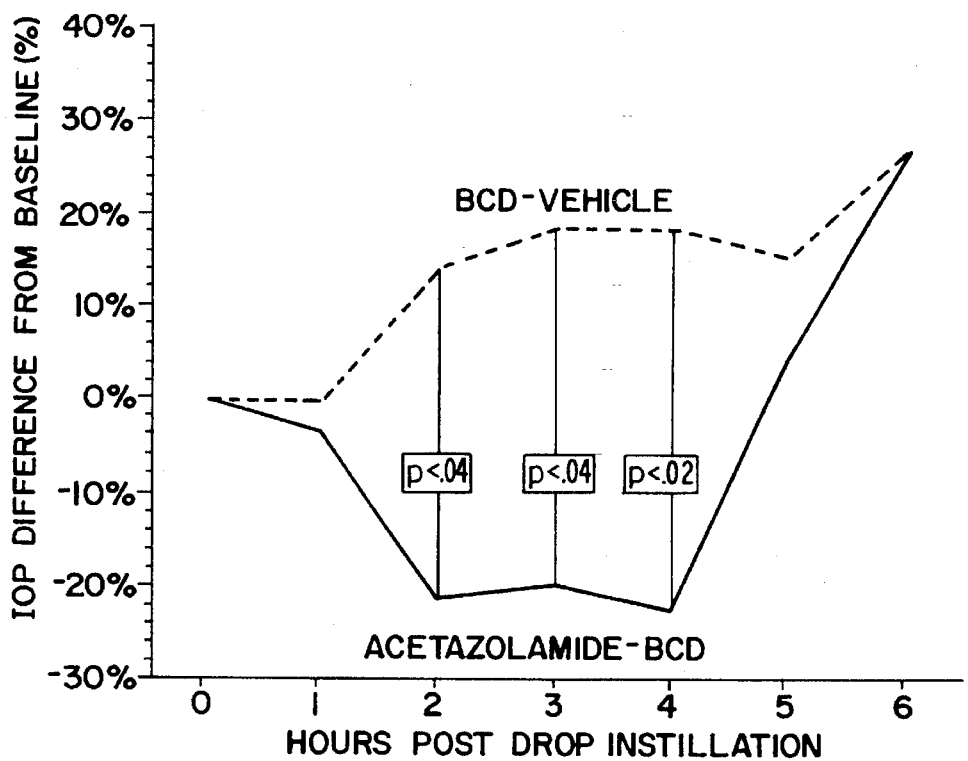
FIG. 2 shows a comparison between the effects of 45% HPBCD and 45% HPBCD in combination with a 1% acetazolamide solution on intraocular pressure (IOP)

Solutions of 1% acetazolamide in 45% HPBCD and 1% Na-acetazolamide in 0.9% NaCl were applied to paired right and left eyes of 10 New Zealand white rabbits (the HPBCD is Type B of Example 3). Intraocular pressure was measured with a Perkins applanation tonometer at hourly intervals until all pressures returned to baseline. As seen from FIG. 1, acetazolamide in 45% HPBCD resulted in a 25% reduction of IOP with return to baseline at approximately 6 hours ($p<0.01$ by paired t-test). In contrast, the Na-acetazolamide in NaCl preparation was associated with only a transient, non-statistically significant lowering of intraocular pressure. As a further control, the acetazolamide/HPBCD preparation was compared with 45% HPBCD alone (control). As before, the acetazolamide/HPBCD preparation resulted in a 25% reduction of intraocular pressure, as compared with the control (FIG. 2). This example shows the value of high-viscosity preparations of HPBCD in solubilizing and increasing the bioavailability of sparingly water-soluble drugs, such as carbonic anhydrase inhibitors.

Example 3

In order to assess the efficiency of 3 different commercially available preparations of HPBCD, the maximum solubility of acetazolamide (maximum solubility in water: 0.1%) was determined for each. The three sources of HPBCD were (A) Roquette (RE No. 446601), (B) American Maize ("Encapsin"), and (C) Wacker Chemical (BetaW7, HP0.9). The Roquette material gave a maximum solubility of 0.1%, the American Maize product gave 1%, and the Wacker product gave a maximum solubility of 1.8%. This example shows that the use of β-cyclodextrin can increase the maximum solubility of carbonic anhydrase inhibitor in topically active preparations.

Example 4

Figure 3:
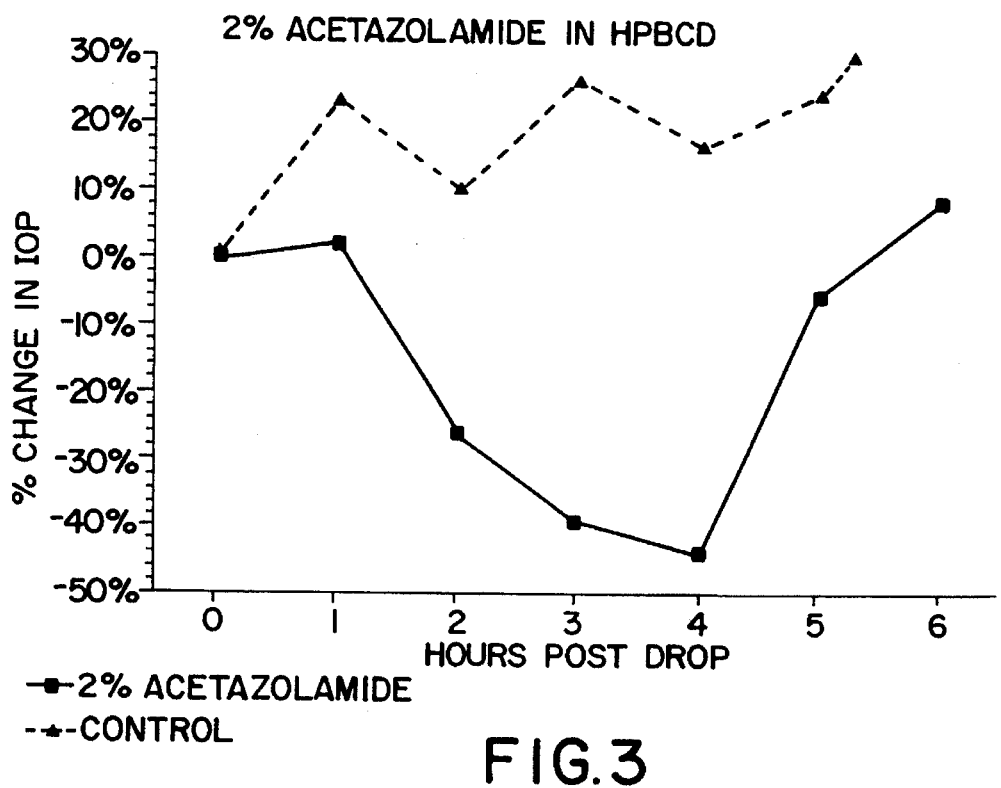
FIG. 3 shows the effect of a 2% acetazolamide solution, alone and in combination with 45% high efficiency HPBCD, on intraocular pressure (IOP) when administered topically to the eye.

Solutions of 1.8% acetazolamide in 45% HPBCD (compound "C" of Example 3) and HPBCD alone (control) were applied to paired right and left eyes of New Zealand white rabbits. Intraocular pressure was measured by applanation tonometry hourly for six hours. Compared with the control eye, intraocular pressure was reduced 60% in the eye treated with 1.8% acetazolamide in β-cyclodextrin (FIG. 3). The pressure reduction achieved is more than twice that achieved with a 1% solution of acetazolamide in normal-efficiency cyclodextrin and far surpasses that which may be achieved with maximally tolerated systemic administration of acetazolamide.

Example 5

Figure 4:
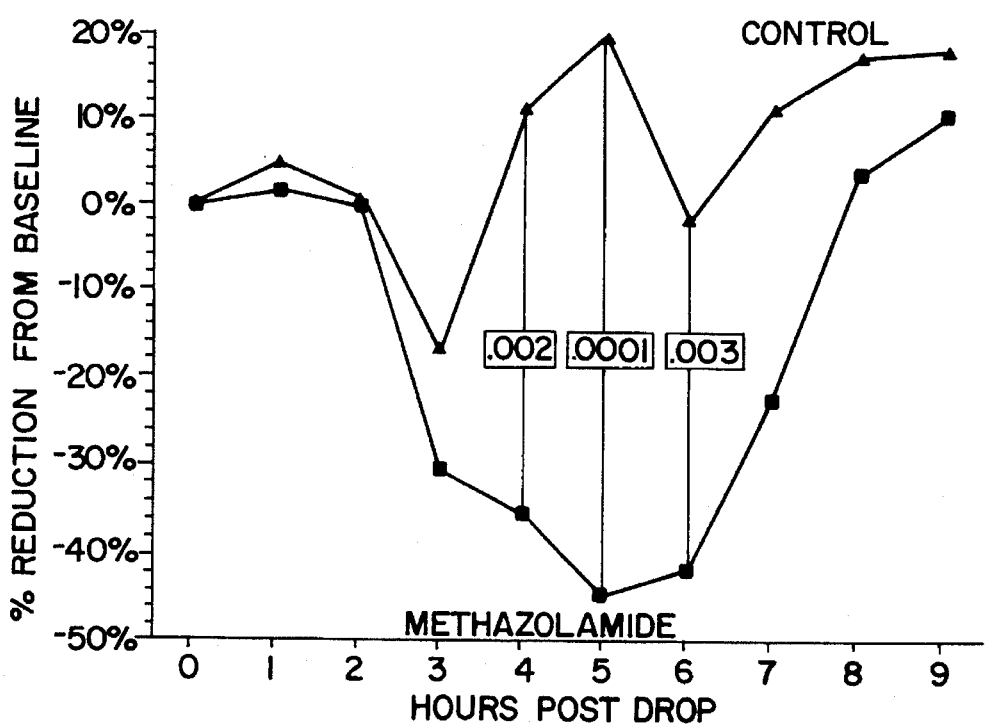
FIG. 4 shows the effect of topical administration of a 1% methazolamide solution combined with 45% HPBCD on intraocular pressure (IOP).

Solutions of 1% methazolamide in 45% HPBCD and the HPBCD alone (control) were applied to paired right and left eyes of New Zealand white rabbits. Intraocular pressure was measured by applanation tonometry until pressures returned to baseline. Compared with the control eye, 1% methazolamide resulted in a 60% reduction in pressure, with return to baseline at 8 hours. These results are shown in FIG. 4. This example illustrates that, when dissolved in HPBCD, methazolamide is more potent and has longer duration of effect than does acetazolamide.

Example 6

45% (w/v) aqueous solutions of 2-hydroxypropyl-β-cyclodextrin using either source A or B (see Example 3) were prepared, and the maximum solubilities of phenoltetrabromphthalein and of cholesterol were determined per 5.0 ml of solution using standard techniques. Phenoltetrabromphthalein concentration was determined spectrophotometrically at 580 mμ. Cholesterol concentration was determined by both GLC and by liquid scintillation counting using cholesterol of known specific activity. The data are shown below, along with a summary of data from other examples.

| | Maximum Solubility and Guest/Host Molar Ratios of various compounds in 45% Hydroxypropyl-β-Cyclodextrin | | | | | | |
|---|---|---|---|---|---|---|---|
| | Phenol-tetrabrom-phthalein | | Choles-terol | | Aceta-zolamide | | Metha-zolamide | |
| β-Cyclo-dextrin | μg/ml | ratio | mg/ml | ratio | mg/ml | ratio | mg/ml | ratio |
| A (Roquette) | 11.1 | .007 | 0.08 | .0015 | >5 | | >5 | |
| B (A. Maize) | 12.5 | .008 | 4.3 | .038 | 20 | 0.31 | 10 | 0.14 |
| C (Wacker) | — | — | 20[a] | .16 | 20 | 0.31 | .21 | .21 |

[a]26-hydroxy cholesterol used in place of cholesterol

Example 7

2.25 g of Wacker 2-hydroxypropyl-β-cyclodextrin (Source C of Example 3) was dissolved in $D_2O$ to give a final volume of 5.0 ml. 100 mg of palmitic acid was added to the solution and the mixture placed in an ultrasonic water bath at 60° C. for several hours, after which it was brought to room temperature and filtered through an 0.22 mµ millipore filter to obtain a clear solution. 3.0 ml of the solution was centrifuged at 100,000× g for 3 hours in a Beckman TL-100 centrifuge. Following centrifugation, aliquots of approximately 1.0 ml were removed from the tube to give upper, middle and lower fractions. A 0.1 ml aliquot from each fraction was pipetted into a tube and 1 mg of cholesterol added as an internal standard. Each tube was then partitioned between ethyl acetate and water to extract all of the palmitic acid and internal standard. The amount of palmitic acid in each aliquot was then determined by GLC using a flame detector.

| Fraction | Palmitic Acid µg/0.1 ml |
|---|---|
| Upper | 41.0 |
| Middle | 34.0 |
| Lower | 23.4 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. An ophthalmic eye drop dispenser comprising a topical, ophthalmic composition comprising an ophthalmically effective amount of carbonic anhydrase inhibitor and an amount of amorphous β-cyclodextrin effective in increasing the bioavailability of the carbonic anhydrase inhibitor when coadministered topically to the eye.

2. An ophthalmic eye drop dispenser comprising a topical, ophthalmic composition comprising an ophthalmically effective amount of carbonic anhydrase inhibitor and an amount of amorphous β-cyclodextrin effective in increasing the solubility of the carbonic anhydrase inhibitor in the composition in comparison to its solubility in the absence of the amorphous β-cyclodextrin.

3. The eye drop dispenser of claim 1, wherein the carbonic anhydrase inhibitor is a heterocyclic sulfonamide.

4. The eye drop dispenser of claim 3, wherein the heterocyclic sulfonamide is acetazolamide or methazolamide.

5. The eye drop dispenser of claim 4, wherein the amount of acetazolamide or methazolamide is effective in reducing intraocular pressure by 20% or more when topically administered in the eye of a person.

6. The eye drop dispenser of claim 5, wherein the amount of acetazolamide is about 0.1 to about 3.5 w/v %.

7. The eye drop dispenser of claim 1, wherein the β-cyclodextrin is hydroxypropyl-β-cyclodextrin.

8. The eye drop dispenser of claim 7, wherein the amount of hydroxypropyl-β-cyclodextrin is about 40–60 w/v %.

9. The eye drop dispenser of claim 1, wherein the β-cyclodextrin derivative is hydroxypropyl-β-cyclodextrin and the carbonic anhydrase inhibitor is acetazolamide or methazolamide.

10. The eye drop dispenser of claim 9, wherein the amount of hydroxypropyl-β-cyclodextrin is about 40–60 w/v %.

11. A method of treating an eye disorder treatable by administering a carbonic anhydrase inhibitor, comprising topically administering to an eye in need of such treatment a topical, ophthalmic composition comprising an ophthalmically effective amount of carbonic anhydrase inhibitor and an amount of amorphous β-cyclodextrin effective in increasing the bioavailability of the carbonic anhydrase inhibitor when topically administered to the eye.

12. The method of claim 11 for inhibiting fluid secretion in the eye or treating an intraocular pressure disorder.

13. The method of claim 11 for treating glaucoma.

14. The method of claim 11, wherein the carbonic anhydrase inhibitor is a heterocyclic sulfonamide.

15. The method of claim 14, wherein the heterocyclic sulfonamide is acetazolamide or methazolamide.

16. The method of claim 11, wherein the β-cyclodextrin is hydroxypropyl-β-cyclodextrin.

17. The method of claim 16, wherein the amount of hydroxypropyl-β-cyclodextrin is about 40–60 w/v %.

18. The method of claim 17, wherein the carbonic anhydrase inhibitor is a heterocyclic sulfonamide.

19. The method of claim 11, wherein the β-cyclodextrin is hydroxypropyl-β-cyclodextrin and the carbonic anhydrase inhibitor is acetazolamide or methazolamide.

20. The method of claim 19 for treating glaucoma.

21. A topical ophthalmic composition comprising an ophthalmically effective amount of carbonic anhydrase inhibitor and 40–60 w/v % of amorphous β-cyclodextrin, said amount of β-cyclodextrin being effective to increase the bioavailability of the carbonic anhydrase inhibitor upon topical administration.

22. A composition of claim 21, wherein the β-cyclodextrin is hydroxypropyl-β-cyclodextrin.

23. A composition of claim 22, wherein the carbonic anhydrase inhibitor is acetazolamide or methazolamide.

24. The composition of claim 22, wherein the carbonic anhydrase inhibitor is a heterocyclic sulfonamide.

25. A composition of claim 21, wherein the carbonic anhydrase inhibitor is acetazolamide or methazolamide.

26. A composition of claim 21, not useful for parenteral administration.

27. A method of treating an eye disorder treatable by administering to an eye in need of such treatment an ophthalmically active agent, comprising topically administering to the eye a topical, ophthalmic composition comprising an effective amount of ophthalmically active agent effective in treating said disorder and an amount of hydroxypropyl-β-cyclodextrin effective in increasing the bioavailability of the ophthalmically active agent when topically administered to the eye.

28. A method of claim 27, wherein the amount of hydroxypropyl-β-cyclodextrin is the amount of about 40–60 w/v %.

29. A topical ophthalmic applicator comprising a topical, ophthalmic composition comprising an ophthalmically effective amount of carbonic anhydrase inhibitor and an amount of amorphous β-cyclodextrin effective in increasing the bioavailability of the carbonic anhydrase inhibitor when coadministered topically to the eye.

* * * * *